United States Patent
Pan et al.

(10) Patent No.: US 11,771,397 B2
(45) Date of Patent: Oct. 3, 2023

(54) METHOD AND DEVICE FOR SIMULTANEOUSLY CARRYING OUT BLOOD FLOW DOPPLER IMAGING AND PULSE DOPPLER IMAGING

(71) Applicant: SONOSCAPE MEDICAL CORP., Guangdong (CN)

(72) Inventors: Xiaochang Pan, Guangdong (CN); Guo Tang, Guangdong (CN); Naizhang Feng, Guangdong (CN); Xuegong Shi, Guangdong (CN); Chi Wang, Guangdong (CN); Linxia Zhang, Guangdong (CN)

(73) Assignee: SONOSCAPE MEDICAL CORP., Guangdong (CN)

( * ) Notice: Subject to any disclaimer, the term of this patent is extended or adjusted under 35 U.S.C. 154(b) by 620 days.

(21) Appl. No.: 16/958,725

(22) PCT Filed: Dec. 20, 2018

(86) PCT No.: PCT/CN2018/122236
§ 371 (c)(1),
(2) Date: Jun. 28, 2020

(87) PCT Pub. No.: WO2019/128825
PCT Pub. Date: Jul. 4, 2019

(65) Prior Publication Data
US 2020/0330067 A1    Oct. 22, 2020

(30) Foreign Application Priority Data
Dec. 29, 2017  (CN) ......................... 201711478370.6

(51) Int. Cl.
*A61B 8/06* (2006.01)
*A61B 8/14* (2006.01)
*A61B 8/08* (2006.01)

(52) U.S. Cl.
CPC ................. *A61B 8/06* (2013.01); *A61B 8/14* (2013.01); *A61B 8/488* (2013.01); *A61B 8/5246* (2013.01)

(58) Field of Classification Search
CPC .. A61B 8/06; A61B 8/14; A61B 8/488; A61B 8/5246
See application file for complete search history.

(56) References Cited

U.S. PATENT DOCUMENTS 6,450,961 B1   9/2002  Shiki et al.
2003/0045795 A1*  3/2003  Bjaerum ............. G01S 7/52034
                                                      600/441

(Continued)

FOREIGN PATENT DOCUMENTS

CN    1440726 A   9/2003
CN   101744643 A   6/2010

(Continued)

OTHER PUBLICATIONS

First Office Action dated Jul. 3, 2020 for Chinese patent application No. 201711478370.6, English translation provided by Global Dossier.

(Continued)

*Primary Examiner* — Boniface Ngathi
(74) *Attorney, Agent, or Firm* — Yue (Robert) Xu; Apex Attorneys at Law, LLP

(57) ABSTRACT

A method for simultaneously performing blood flow Doppler imaging and pulse Doppler imaging includes: sequentially transmitting each transmission sequence group including multiple blood flow sequences and a B-mode sequence thereafter; sequentially receiving a first echo signal group reflected by a tissue area of interest in response to the blood flow sequence; sequentially performing beam composition on the first echo signal group corresponding to the blood flow sequence transmitted each time, to obtain a first multi- (Continued)

beam corresponding thereto; sequentially performing wall filtering on the first multi-beam corresponding to the blood flow sequence transmitted each time, to obtain a second multi-beam corresponding thereto, wherein the second multi-beam is a multi-beam representing a blood flow signal in the first multi-beam; and performing a blood-flow-mode imaging process and a blood flow spectrum imaging process based on sequentially obtained second multi-beams.

12 Claims, 5 Drawing Sheets

(56) References Cited

U.S. PATENT DOCUMENTS

| | | | |
|---|---|---|---|
| 2010/0022884 A1* | 1/2010 | Ustuner | A61B 8/461 |
| | | | 600/453 |
| 2012/0029350 A1 | 2/2012 | Li et al. | |
| 2012/0053461 A1* | 3/2012 | Li | G01S 7/52033 |
| | | | 600/441 |
| 2012/0152021 A1 | 6/2012 | Ma et al. | |
| 2014/0018680 A1 | 1/2014 | Guracar | |
| 2018/0085088 A1 | 3/2018 | Du et al. | |
| 2018/0146952 A1 | 5/2018 | Du et al. | |

FOREIGN PATENT DOCUMENTS

| | | | |
|---|---|---|---|
| CN | 102342848 A | 2/2012 |
| CN | 102342849 A | 2/2012 |
| CN | 102370499 A | 3/2012 |
| CN | 102551791 A | 7/2012 |
| CN | 103142252 A | 6/2013 |
| CN | 103536315 A | 1/2014 |
| CN | 105596032 A | 5/2016 |
| CN | 106102587 A | 11/2016 |
| CN | 106102589 A | 11/2016 |
| CN | 108577891 A | 9/2018 |
| EP | 1826587 A2 | 8/2007 |
| JP | 08229039 A | 9/1996 |

OTHER PUBLICATIONS

Qi Yanan et al.,"Clinical diagnosis and treatment of common diseases(volume One)", Changchun: Jilin Science and Technology Press, Mar. 2017, pp. 88-90.
Duan Zongwen et al., "Clinical Ultrasound Medicine (volume One)",Beijing: Science and Technology Literature Press, Jun. 2017,pp. 45-48.
Second Office Action dated Jan. 14, 2021 for Chinese patent application No. 201711478370.6, English translation provided by Unitalen.
Pang Ning et al., "Enhance the quality of the ultrasound image preliminary explore", Chinese Society of Embodiments. Proceedings of the Twelfth Chinese Conference on Embodiments and Image Analysis, Sep. 1, 2008, p. 469-472.
Ye Weiqiang et al., "Study of Power Doppler Imaging Method with Ultrasonic Plane Wave", Journal of Integration Technology, vol. 4 No. 3, May 15, 2015, p. 79-85.
Qian Yunqiu et al., "Ultrasound Diagnostics", Xi'an: Fourth Military Medical University Press, Jan. 31, 2008, p. 24.
International Search Report for PCT/CN2018/122236 dated Apr. 1, 2019 , ISA/CN.

* cited by examiner

METHOD AND DEVICE FOR SIMULTANEOUSLY CARRYING OUT BLOOD FLOW DOPPLER IMAGING AND PULSE DOPPLER IMAGING

The present application is the US national phase of International Patent Application NO. PCT/CN2018/122236, titled "METHOD AND DEVICE FOR SIMULTANEOUSLY CARRYING OUT BLOOD FLOW DOPPLER IMAGING AND PULSE DOPPLER IMAGING", filed on Dec. 20, 2018, which claims priority to Chinese Patent Application No. 201711478370.6, titled "METHOD AND DEVICE FOR SIMULTANEOUSLY CARRYING OUT BLOOD FLOW DOPPLER IMAGING AND PULSE DOPPLER IMAGING", filed on Dec. 29, 2017, with the China National Intellectual Property Administration, both of which are incorporated herein by reference in their entirety.

FIELD

The present disclosure relates to the field of ultrasonic imaging, and in particular to a method and a device for simultaneously performing blood flow Doppler imaging and pulse Doppler imaging.

BACKGROUND

Ultrasonic blood flow imaging includes B-mode imaging and blood-flow-mode imaging. The B-mode imaging is used to display structural information of tissue. The blood-flow-mode imaging is used to display blood flow velocity and energy information in the tissue. The blood flow velocity and the energy information include an image reflecting the blood flow velocity and energy and a spectrum image reflecting blood flow variation over time.

At present, for the ultrasonic blood flow imaging, an ultrasonic system alternately transmits sequences in a transmission order of a B-mode sequence, a blood flow sequence and a Doppler sequence. In addition, the ultrasonic system composites a frame of B-mode image based on B-mode sequences, composites a frame of blood-flow-mode image based on blood flow sequences and performs a Fourier transform on a multi-beam composited based on Doppler sequences to obtain a spectrum image.

In conventional technologies, a blood-flow-mode image is composited first based on blood flow sequences and then a spectrum image is determined based on Doppler sequences. Therefore, the ultrasonic system can not simultaneously obtain a blood-flow-mode image and a spectrum image at a time.

SUMMARY

In view of the above, a method for simultaneously performing blood flow Doppler imaging and pulse Doppler imaging is provided according to the present disclosure, to enable simultaneous performing of composition of a colorful blood-flow-mode image and determination of a spectrum image, such that an ultrasonic system can simultaneously obtain a blood-flow-mode image and a spectrum image at a time.

A device is further provided according to the present disclosure to enable implementation and application of the above method in practice.

Technical solutions provided according to the present disclosure are described as follows.

A method for simultaneously performing blood flow Doppler imaging and pulse Doppler imaging is provided according to the present disclosure. The method includes:

sequentially transmitting each transmission sequence group, where in each transmission sequence group, a B-mode sequence is transmitted for once and a blood flow sequence is transmitted for multiple times after the B-mode sequence is transmitted;

sequentially receiving a first echo signal group reflected by a tissue area of interest in response to the blood flow sequence transmitted each time in each transmission sequence group;

sequentially performing beam composition on the first echo signal group corresponding to the blood flow sequence transmitted each time, to obtain a first multi-beam corresponding to the blood flow sequence transmitted each time;

sequentially performing wall filtering on the first multi-beam corresponding to the blood flow sequence transmitted each time, to obtain a second multi-beam corresponding to the blood flow sequence transmitted each time, where the second multi-beam is a multi-beam representing a blood flow signal in the first multi-beam; and performing a blood-flow-mode imaging process and a blood flow spectrum imaging process based on sequentially obtained second multi-beams, where performing the blood-flow-mode imaging process includes: determining a frame of blood-flow-mode image based on the second multi-beam corresponding to the blood flow sequence in each transmission sequence group, and performing the blood flow spectrum imaging process includes: determining, based on target sampling point groups corresponding to each first predetermined number of received second multi-beams, a spectrum image of a blood flow in the tissue area of interest corresponding to each position of the target sampling point groups, where a target sampling point group corresponding to each second multi-beam is a sampling point group distributed in multiple rows and multiple columns and obtained by performing a sampling operation on each beam line of the second multi-beam in a predetermined manner.

The B-mode sequence transmitted each time sequentially corresponds to one of a second predetermined number of subareas forming a tissue area, and the method further includes:

sequentially receiving a second echo signal group reflected by a corresponding subarea in response to the B-mode sequence transmitted each time;

sequentially performing multi-beam composition on the second echo signal group corresponding to the B-mode sequence transmitted each time, to obtain a third multi-beam corresponding to the B-mode sequence transmitted each time;

determining, based on the third multi-beam corresponding to the B-mode sequence transmitted each time, a frame of B-mode image of the subarea in the tissue area corresponding to the B-mode sequence transmitted each time; and sequentially updating, in a B-mode image corresponding to the tissue area, a B-mode image of the subarea corresponding to the B-mode sequence transmitted each time.

Determining, based on the target sampling point groups corresponding to each first predetermined number of received second multi-beams, the spectrum image of the blood flow in the tissue area of interest corresponding to each position of the target sampling point groups includes:

performing a sampling operation, in a direction perpendicular to an ultrasonic probe, on each beam line segment with a predetermined length in each beam line of the second multi-beam corresponding to the blood flow sequence transmitted each time in each of transmission sequence groups corresponding to the first predetermined number, to obtain a target sampling point group distributed in multiple rows and multiple columns and corresponding to the blood flow sequence transmitted each time;

performing an interpolation operation, for two target sampling point groups corresponding to two blood flow sequences sharing a same rank in respect of transmission order respectively in each two adjacent transmission sequence groups, on sampling points having a same position in the two target sampling point groups, to obtain an interpolation sampling point group corresponding to the two blood flow sequences sharing the same rank in respect of transmission order; and performing, for transmission sequence groups corresponding to the first predetermined number of second multi-beams, a Fourier transform on sampling points having a same position in the target sampling point groups and in the interpolation sampling point groups corresponding to the transmitted blood flow sequence, to obtain the spectrum image of the blood flow in the tissue area corresponding to each position.

Determining the frame of blood-flow-mode image based on the second multi-beam corresponding to the blood flow sequence in each transmission sequence group includes:

sequentially performing a sampling operation, in a direction perpendicular to an ultrasonic probe, on each beam line segment with a predetermined length in each beam line of each second multi-beam, to obtain a target sampling point group distributed in multiple rows and multiple columns and corresponding to the blood flow sequence transmitted each time in each transmission sequence group;

determining, for two target sampling point groups corresponding to the blood flow sequence transmitted at each two adjacent times and based on beam line segments to which two sampling points having a same position respectively in the two target sampling point groups belongs, a velocity of a blood flow at each same position, to obtain a velocity of a blood flow corresponding to the blood flow sequence transmitted at each two adjacent times at each same position;

determining, based on the velocity of the blood flow corresponding to the blood flow sequence transmitted at each two adjacent times at each same position, a movement velocity of a blood flow in the tissue area of interest corresponding to each same position; and determining, based on a correspondence relationship between each same position in the tissue area of interest and the movement velocity of the blood flow, the frame of blood-flow-mode image.

The method further includes:

compositing the blood-flow-mode image and the B-mode image to obtain a blood flow image; and displaying the blood flow image and a spectrum image of a blood flow at a user-specified position in the blood flow image.

The transmitted B-mode sequence and the blood flow sequence are transmitted in a non-focusing manner.

A device is further provided according to the present disclosure. The device includes a transmission module, a multi-beam composition module, a wall filtering module and a blood-flow-mode imaging module.

The transmission module is configured to, when a transceiving switch is in a transmitting state, sequentially transmit each transmission sequence group, where in each transmission sequence group, a B-mode sequence is transmitted for once and a blood flow sequence is transmitted for multiple times after the B-mode sequence is transmitted.

The multi-beam composition module is configured to, when the transceiving switch is in a receiving state, sequentially receive a first echo signal group reflected by a tissue area of interest in response to the blood flow sequence transmitted each time in each transmission sequence group.

The multi-beam composition module is further configured to sequentially perform beam composition on the first echo signal group corresponding to the blood flow sequence transmitted each time, to obtain a first multi-beam corresponding to the blood flow sequence transmitted each time.

The wall filtering module is configured to sequentially perform wall filtering on the first multi-beam corresponding to the blood flow sequence transmitted each time, to obtain a second multi-beam corresponding to the blood flow sequence transmitted each time, where the second multi-beam is a multi-beam representing a blood flow signal in the first multi-beam.

The blood-flow-mode imaging module is configured to perform a blood-flow-mode imaging process and a blood flow spectrum imaging process based on sequentially obtained second multi-beams, where performing the blood-flow-mode imaging process includes: determining a frame of blood-flow-mode image based on the second multi-beam corresponding to the blood flow sequence in each transmission sequence group, and performing the blood flow spectrum imaging process includes: determining, based on target sampling point groups corresponding to each first predetermined number of received second multi-beams, a spectrum image of a blood flow in the tissue area of interest corresponding to each position of the target sampling point groups, where a target sampling point group corresponding to each second multi-beam is a sampling point group distributed in multiple rows and multiple columns and obtained by performing a sampling operation on each beam line of the second multi-beam in a predetermined manner.

The B-mode sequence transmitted each time sequentially corresponds to one of a second predetermined number of subareas forming a tissue area. The transmission module is further configured to sequentially receive a second echo signal group reflected by a corresponding subarea in response to the B-mode sequence transmitted each time. The multi-beam composition module is further configured to sequentially perform multi-beam composition on the second echo signal group corresponding to the B-mode sequence transmitted each time, to obtain a third multi-beam corresponding to the B-mode sequence transmitted each time.

The device further includes a B-mode imaging module.

The B-mode imaging module is configured to determine, based on the third multi-beam corresponding to the B-mode sequence transmitted each time, a frame of B-mode image of the subarea in the tissue area corresponding to the B-mode sequence transmitted each time, and sequentially update, in a B-mode image corresponding to the tissue area, a B-mode image of the subarea corresponding to the B-mode sequence transmitted each time.

The device further includes a display module.

The display module is configured to composite the blood-flow-mode image and the B-mode image to obtain a blood flow image; and display the blood flow image and a spectrum image of a blood flow at a user-specified position in the blood flow image.

The B-mode sequence and the blood flow sequence are transmitted by the transmission module in a non-focusing manner.

Beneficial effects of the present disclosure are described as following.

In the embodiments of the present disclosure, sequences in each transmission sequence group are sequentially transmitted, where in each transmission sequence group, a B-mode sequence is transmitted for once and a blood flow sequence is transmitted for multiple times after the B-mode sequence is transmitted. Multi-beam composition is performed based on the blood flow sequence transmitted each time in each transmitted transmission sequence group. Wall filtering is performed on a multi-beam formed by the multi-beam composition to obtain a second multi-beam corresponding to the blood flow sequence transmitted each time. Next, a frame of blood-flow-mode image is determined based on the second multi-beam corresponding to the blood flow sequence in each transmission sequence group. In addition, a spectrum image of a blood flow in the tissue area of interest corresponding to each location of target sampling point groups is determined based on the target sampling point group corresponding to each first predetermined number of received second multi-beams. In this way, one frame spectrum image can be obtained while multiple frames of blood flow image are generated. Further, an ultrasonic system according to the embodiments of the present disclosure can simultaneously obtain a blood-flow-mode image and a spectrum image of blood flow velocity at a time.

BRIEF DESCRIPTION OF THE DRAWINGS

In order to more clearly describe the technical solutions in the embodiments of the present disclosure or the technical solutions in the conventional technology, drawings to be used in the description of the embodiments of the present disclosure or the conventional technology are briefly described hereinafter. It is apparent that the drawings described below show merely the embodiments of the present disclosure, and those skilled in the art may obtain other drawings according to the provided drawings without any creative effort.

DETAILED DESCRIPTION OF EMBODIMENTS

Technical solutions of embodiments of the present disclosure are clearly and completely described below in conjunction with the drawings of the embodiments of the present disclosure. Apparently, the embodiments described in the following are only some embodiments of the present disclosure, rather than all the embodiments. Any other embodiments obtained by those skilled in the art based on the embodiments in the present disclosure without any creative effort fall within the protection scope of the present disclosure.

The inventor found in a study that in conventional technologies, transmission sequences are transmitted to a tissue area in such an order that a B-mode sequence is transmitted once, then a blood flow sequence is transmitted for multiple times and next a Doppler sequence is transmitted for multiple times. A frame of B-mode image is determined based on an echo signal group reflected by a tissue area in response to each transmitted B-mode sequence, a frame of blood flow image is determined based on multiple echo signal groups reflected by a tissue area of interest in response to the blood flow sequence transmitted for respective multiple times, and next, a spectrum image of a blood flow in the tissue area of interest is determined based on multiple echo signal groups reflected by the tissue area of interest in response to the Doppler sequence transmitted for respective multiple times. For any transmission sequence group, the Doppler sequence for determining the spectrum image is transmitted after the blood flow sequence for determining the blood flow image is transmitted. Therefore, the blood flow image and the spectrum image can not be obtained simultaneously. By contrast, in an embodiment of the present disclosure, each transmission sequence group only includes a B-mode sequence and a blood flow sequence transmitted for multiple times. A blood flow image is determined based on the blood flow sequence transmitted for multiple times, and a spectrum image of a blood flow in the tissue area of interest corresponding to each location of target sampling point groups is determined based on the target sampling point groups corresponding to received second multi-beam corresponding to each first predetermined number of blood flow sequences. Thus, an ultrasonic system can simultaneously obtain a blood-flow-mode image and a spectrum image at a time.

Figure 1:
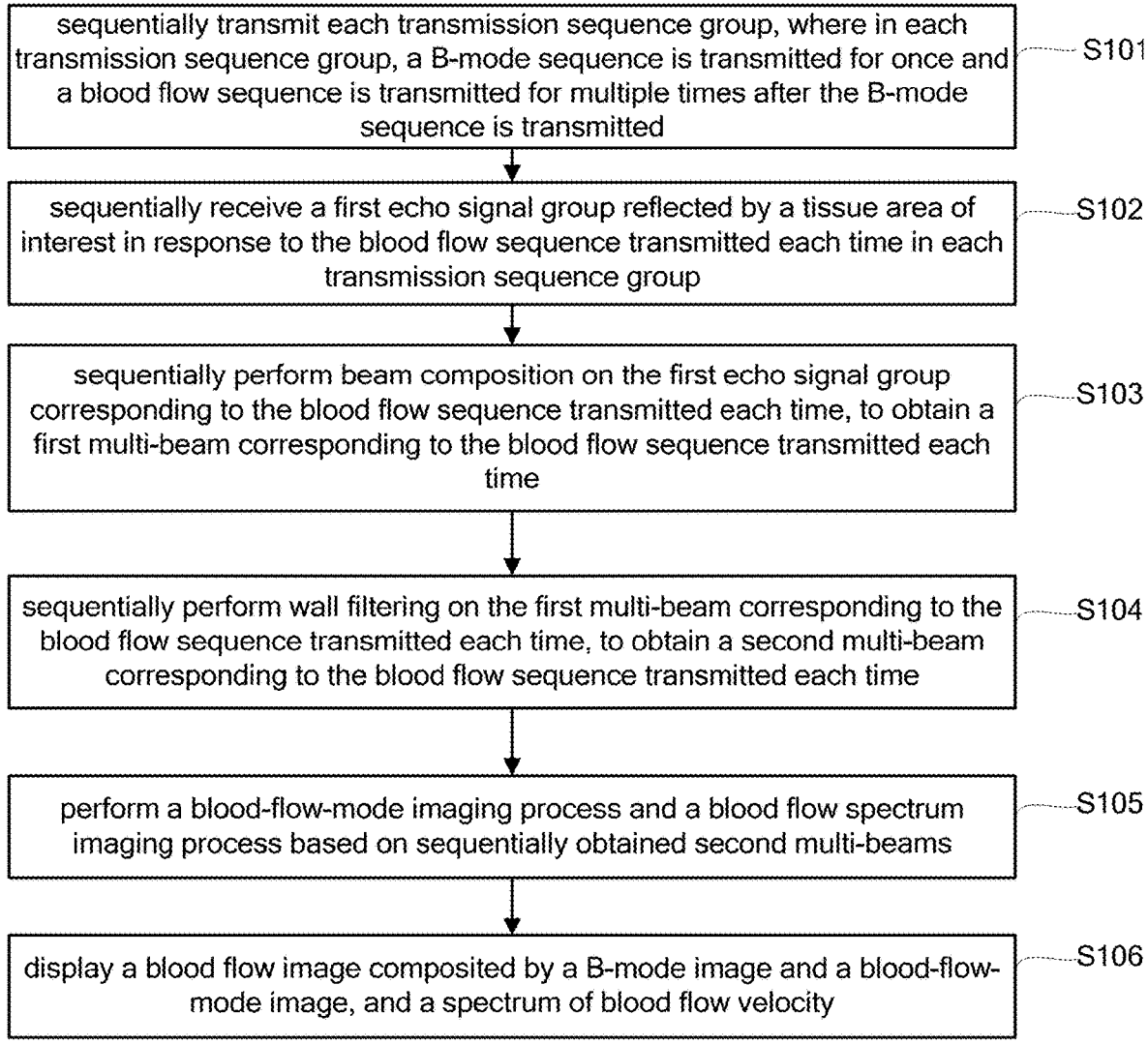
FIG. 1 is a flowchart of a method for simultaneously performing blood flow Doppler imaging and pulse Doppler imaging according to an embodiment of the present disclosure.

Specifically, in order to simultaneously perform blood flow Doppler imaging and pulse Doppler imaging, reference is made to FIG. 1, which shows a flowchart of a method for simultaneously performing blood flow Doppler imaging and pulse Doppler imaging according to of an embodiment the present disclosure. The method according to the embodiment may include steps S101 to S106.

In step S101, each transmission sequence group is sequentially transmitted, where in each transmission sequence group, a B-mode sequence is transmitted for once and a blood flow sequence is transmitted for multiple times after the B-mode sequence is transmitted.

Figure 2:
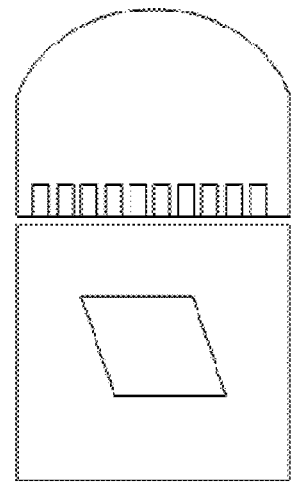
FIG. 2 (*a*) is a schematic diagram showing that an ultrasonic device transmits a blood flow sequence to a blood flow area of interest (a blood flow imaging area) and FIG. 2(*b*) is a schematic diagram shows that the ultrasonic device transmits a B-mode sequence to a B-mode imaging area according to the present disclosure.
Figure 2:
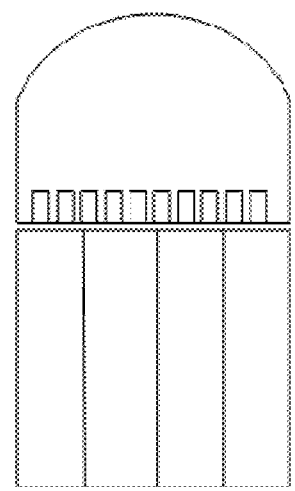

In the present embodiment, a transmission module in an ultrasonic device sequentially transmits sequences in each transmission sequence group, where in each transmission sequence group, a B-mode sequence is transmitted for once and a blood flow sequence is transmitted for multiple times after the B-mode sequence is transmitted. In the embodiment, the blood flow sequence in each transmission sequence group is transmitted by an array element of an ultrasonic probe corresponding to a tissue area of interest, as shown in FIG. 2(a). In FIG. 2 (a), the tissue area of interest is a part of a tissue area within a range of an acoustic beam generated by the ultrasonic probe. In this case, with respect to each transmission sequence group, the blood flow sequence transmitted each time is transmitted by the array element of the ultrasonic probe corresponding to the tissue area of interest.

In addition, in the present embodiment, the B-mode sequence in each transmission sequence group corresponds to one of at least two subareas forming a tissue area covered by the ultrasonic probe. The B-mode sequence in each of sequentially transmitted transmission sequence groups sequentially corresponds to a subarea forming the tissue area. As shown in FIG. 2 (b), the tissue area is divided into four subareas with a same width, which respectively are a first subarea, a second subarea, a third subarea and a fourth subarea from left to right. In this case, a B-mode sequence in a first transmission sequence group corresponds to the first subarea in the tissue area, a B-mode sequence in a second transmission sequence group corresponds to the second subarea . . . a B-mode sequence in a fourth transmission sequence group corresponds to the fourth subarea, a B-mode sequence in a fifth transmission sequence group corresponds to the first subarea, and so forth. A B-mode sequence in a transmission sequence group is transmitted by an ultrasonic probe corresponding to a subarea corresponding to the B-mode sequence in the transmission sequence group among ultrasonic probes. In addition, in the present embodiment, the B-mode sequence and the blood flow sequence transmitted each time are transmitted in a non-focusing manner. That is, a transmitted sequence is propagated in tissue along a plane or in a diverging manner.

In step S102, a first echo signal group reflected by the tissue area of interest in response to the blood flow sequence transmitted each time in each transmission sequence group is sequentially received.

In the present embodiment, sequences in each transmission sequence group are sequentially transmitted. For each transmission sequence group, echo signals are reflected by the tissue area in response to each transmitted sequence. In order for ease of description of a processing procedure of the echo signals reflected by the tissue area in response to a transmitted sequence according to the present embodiment, one transmission sequence group is taken as an example for purpose of description in the present embodiment. That is, unless indicated to the contrary, the following steps are meant for processing on sequences of one transmission sequence group.

For convenience of description, the echo signals reflected by the tissue area of interest in response to the blood flow sequence transmitted each time in each transmission sequence group are collectively referred to as first echo signal group. Therefore, the blood flow sequence transmitted each time corresponds to a first echo signal group. Next, in the present step, a first echo signal group corresponding to the blood flow sequence transmitted each time is sequentially received. In practice, the ultrasonic device has a transceiving switch. When the transceiving switch is in a transmitting state, the transmission module in the ultrasonic device transmits sequences. When the transmission module switch is in a receiving state, a multi-beam composition module functions as a receiving module configured to receive an echo signal group reflected by the tissue in response to a transmitted sequence.

In the present embodiment, echo signals reflected by a corresponding subarea in response to the B-mode sequence transmitted each time are further received. For convenience of description, in the present embodiment, the echo signals reflected by the corresponding in response to the B-mode sequence transmitted each time are collectively referred to as second echo signal group. The second echo signal group corresponding to the B-mode sequence transmitted each time is sequentially received.

In step S103, beam composition is sequentially performed on the first echo signal group corresponding to the blood flow sequence transmitted each time, to obtain a first multi-beam corresponding to the blood flow sequence transmitted each time.

After the first echo signal group corresponding to the blood flow sequence transmitted each time is received, in the present step, multi-beam composition is sequentially performed on the first echo signal group corresponding to the blood flow sequence transmitted each time, to obtain a multi-beam corresponding to the first echo signal group corresponding to the blood flow sequence transmitted each time. For convenience of description, in the present embodiment, the multi-beam composited by the first echo signal group corresponding to the blood flow sequence transmitted each time is uniformly referred to as first multi-beam.

In the present embodiment, in addition to performing beam composition on the first echo signal group corresponding to the blood flow sequence transmitted each time in the transmission sequence group, multi-beam composition is performed on the second echo signal group corresponding to the transmitted B-mode sequence. For convenience of description, in the present embodiment, a multi-beam composited by the second echo signal group corresponding to the B-mode sequence transmitted each time is uniformly referred to as third multi-beam.

In step S104, wall filtering is sequentially performed on the first multi-beam corresponding to the blood flow sequence transmitted each time, to obtain a second multi-beam corresponding to the blood flow sequence transmitted each time, where the second multi-beam is a multi-beam representing a blood flow signal in the first multi-beam.

After the first multi-beam corresponding to the blood flow sequence transmitted each time is obtained, where the first multi-beam is an IQ signal group including multiple IQ signals and each IQ signal includes a tissue signal and a blood flow signal, in the present step, it is required to extract the blood flow signal in each first multi-beam. Specifically, wall filtering is sequentially performed on the first multi-beam corresponding to the blood flow sequence transmitted each time. The essence of the wall filtering is performing high-pass filtering on signals in the first multi-beam. As the tissue signal and the blood flow signal included in the signals in the first multi-beam have different frequency characteristics, the blood flow signal can be extracted from the first multi-beam by a predetermined cut-off frequency.

Specifically, in the present embodiment, the wall filtering may be performed on the first multi-beam with a polynomial regression filter. The high-pass filtering may be performed with the polynomial regression filter on multiple first multi-beams respectively corresponding to the blood flow sequence transmitted for the multiple times in the transmission sequence group through the following procedures. The polynomial regression filter first performs polynomial fitting on multiple IQ signals at different time points and having a same position respectively in the multiple first multi-beams, to obtain a fitted signal corresponding to each same position in the multiple first multi-beams. Then, for each IQ signal in each first multi-beam, a value of a fitted signal at a position of the IQ signal is subtracted from a value of the IQ signal, to obtain a target signal corresponding to each position in the first multi-beam. For convenience of description, in the present embodiment, a multi-beam including target signals corresponding to all positions in each first multi-beam is referred to as second multi-beam. In this case, the second multi-beam corresponding to the blood flow sequence transmitted each time is obtained.

In step S105, a blood-flow-mode imaging process and a blood flow spectrum imaging process are performed based on sequentially obtained second multi-beams For each transmission sequence group, after the second multi-beam corresponding to the blood flow sequence transmitted each time in the transmission sequence group is obtained, in the present step, a blood-flow-mode imaging process and a blood flow spectrum imaging process are performed based on the sequentially obtained second multi-beams. The blood-flow-mode imaging process includes steps A1 to A4.

In step A1, a sampling operation is sequentially performed, in a direction perpendicular to an ultrasonic probe, on each beam line segment with a predetermined length in each beam line of each second multi-beam, to obtain a target sampling point group distributed in multiple rows and multiple columns and corresponding to the blood flow sequence transmitted each time in each transmission sequence group.

In this step, for the second multi-beam corresponding to the blood flow sequence transmitted each time, sampling is sequentially performed, in a direction perpendicular to the ultrasonic probe, on each beam line of the second multi-beam, to obtain the target sampling point group distributed in multiple rows and multiple columns and corresponding to the second multi-beam. For convenience of description, in the present embodiment, the sampling point group corresponding to the second multi-beam corresponding to the blood flow sequence transmitted each time is uniformly referred to as target sampling point group.

In step A2, for two target sampling point groups corresponding to the blood flow sequence transmitted at each two adjacent times, a velocity of a blood flow at each same position is determined based on beam line segments to which two sampling points having a same position in the two target sampling point groups belongs, to obtain a velocity of a blood flow corresponding to the blood flow sequence transmitted at each two adjacent times at each same position.

After the sampling point group corresponding to the blood flow sequence transmitted each time is obtained, in the present step, by a transmission order of the blood flow sequence, for two target sampling point groups corresponding to the blood flow sequence transmitted at each two adjacent times, there are two sampling points sharing a same position in the two target sampling point groups. Based on two beam line segments respectively in two second multi-beam, in which the two sampling points sharing each same position are located, a velocity of a blood flow in the tissue area of interest corresponding to each same position is determined according to equation (1):

$$v = \frac{c}{4\pi f_0} \arctan\left(\frac{\sum_{m=0}^{M-1} Q(m,n)I(m,n) - \sum_{m=0}^{M-1} I(m,n)Q(m,n)}{\sum_{m=0}^{M-1} I(m,n)Q(m,n) - \sum_{m=0}^{M-1} Q(m,n)I(m,n)}\right) \quad (1)$$

In above equation (1), v represents a velocity of a blood flow in the tissue area of interest corresponding to a current sampling point, c represents a velocity of sound in biological tissue, $f_0$ represents a center frequency of the transmitted blood flow sequence, I and Q respectively represents a real part and an imaginary part of the IQ signal in the second multi-beam, m represents a point in an axial direction of the IQ signal, M represents an axial length of a signal used to calculate a velocity of a blood flow corresponding to a sampling point and n represents a transmission serial number of a current blood flow sequence.

For example, supposing in one transmission sequence group the blood flow sequence transmitted for the multiple times is respectively T1, T2, T3, T4, T5, T6, T7, and T8, accordingly in the present step, a velocity of a blood flow in the tissue area of interest at sampling points sharing each same position in target sampling point groups corresponding to the blood flow sequence transmitted at each two adjacent times is sequentially calculated, the blood flow sequence transmitted at each two adjacent times being T1 and T2, T2 and T3, T3 and T4, T5 and T6, T6 and T7, and T7 and T8.

In the present embodiment, after the velocity of the blood flow in the tissue area of interest corresponding to the sampling points sharing each same position is sequentially obtained for the target sampling point groups corresponding to the blood flow sequence transmitted at each two adjacent times, it is further required to extract a blood flow position from the tissue area of interest for the blood flow sequence transmitted each time. Specifically, a difference between the first multi-beam and the second multi-beam corresponding to the blood blow sequence transmitted each time may be calculated, and then the blood flow position corresponding to the blood blow sequence transmitted each time is obtained by a threshold segmentation method. Generally, there may be some holes in the extracted blood flow position, because there is no blood flow to scatter sub-signals in the tissue area during transmission of the blood flow sequence though there are vessels in these places. In order to fill the holes, it is generally required to perform low-pass filtering or a morphology closure operation on a binary image of the extracted blood flow position.

In step A3, a movement velocity of a blood flow in the tissue area of interest corresponding to each same position is determined based on the velocity of the blood flow corresponding to the blood flow sequence transmitted at each two adjacent times at each same position.

After the velocity of the blood flow corresponding to the blood flow sequence transmitted at each two adjacent times at each same position is obtained, in the present step, the movement velocity of the blood flow in the tissue area of interest corresponding to each position is determined based on the velocity of the blood flow corresponding to the blood flow sequence transmitted at each two adjacent times at each same position, for example, based on a movement velocity of a blood flow in the tissue area of interest corresponding to sampling points at each position for target sampling point groups corresponding to the blood flow sequence transmitted at each two adjacent times, the blood flow sequence transmitted at each two adjacent times being T1 and T2, T2 and T3, T3 and T4, T5 and T6, T6 and T7, and T7 and T8.

In step A4, a frame of blood-flow-mode image is determined based on a correspondence relationship between each same position in the tissue area of interest and the movement velocity of the blood flow.

After the movement velocity of the blood flow in the tissue area of interest corresponding to each same position is obtained, a correspondence relationship between position and movement velocity of blood flow is obtained. In the present embodiment, a frame of blood flow-mode image is determined based on the correspondence relationship.

In the present embodiment, a blood flow spectrum imaging process is further performed. The blood flow spectrum imaging process may include: determining, based on target sampling point groups corresponding to each first predetermined number of received second multi-beams from the sequentially obtained second multi-beams, a spectrum image of a blood flow in the tissue area of interest corresponding to each position of the target sampling point groups, where the spectrum image of the blood flow in the tissue area of interest corresponding to each position of the target sampling point groups is determined based on transmission sequence groups corresponding to each first predetermined number of received second multi-beams.

In step S106, a blood flow image composited by a B-mode image and a blood-flow-mode image, and a spectrum of blood flow velocity are displayed.

A frame of B-mode image and a frame of blood-flow-mode image are obtained based on one transmission sequence group, and a spectrum corresponding to a blood flow velocity at each position in the tissue area of interest is obtained based on the target sampling point groups corresponding to the first predetermined number of second multi-beams. Next, in the present step, the obtained B-mode image, blood-flow-mode image and spectrum of blood flow velocity are displayed. Specifically, for each transmission sequence group, a blood flow image composited by a B-mode image and a blood-flow-mode image is displayed. In addition, for transmission sequence groups corresponding to the first predetermined number of second multi-beams, a spectrum image of a blood flow at a user-specified position in the blood flow image is displayed.

Figure 3:
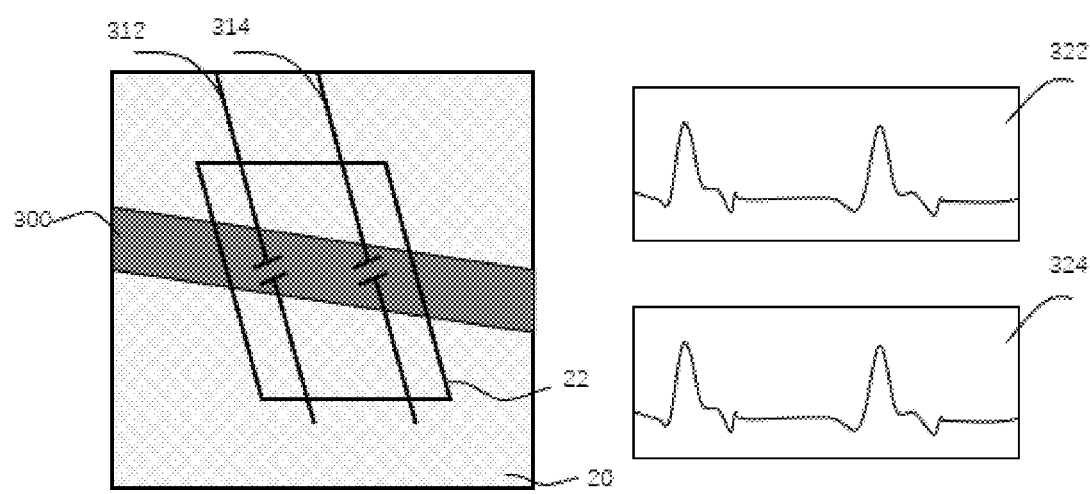
FIG. 3 is a schematic diagram showing a blood-flow-mode image, a B-mode image and a spectrum image at a user-specified position in the blood flow imaging area according to the present disclosure.

FIG. 3 shows a schematic diagram of a blood-flow-mode image, a B-mode image and a spectrum image at a blood flow position displayed by a display unit in the present step.

In FIG. 3, the reference number 20 denotes the B-mode image, the reference number 22 denotes the blood-flow-mode image corresponding to the tissue area of interest, the reference number 300 denotes a blood vessel in the tissue, and the reference number 312 and the reference number 314 respectively denote two blood flow positions in the blood vessel. The spectrum image denoted by the reference number 322 is a spectrum image of the blood flow position denoted by the reference number 312, and the spectrum image denoted by the reference number 324 is a spectrum image of the blood flow position denoted by the reference number 314.

It should be noted that in the present embodiment, the B-mode sequence transmitted in each transmission sequence group corresponds to one frame of B-mode image. After a B-mode image corresponding to a subarea is obtained, the subarea, in a B-mode image corresponding to the entire tissue area, corresponding to the current B-mode sequence is updated with the B-mode image currently obtained.

In the embodiments of the present disclosure, sequences in each transmission sequence group are sequentially transmitted, where in each transmission sequence group, a B-mode sequence is transmitted for once and a blood flow sequence is transmitted for multiple times after the B-mode sequence is transmitted. Multi-beam composition is performed based on the blood flow sequence transmitted each time in each transmitted transmission sequence group. Wall filtering is performed on a multi-beam formed by the multi-beam composition to obtain a second multi-beam corresponding to the blood flow sequence transmitted each time. Next, a frame of blood-flow-mode image is determined based on the second multi-beam corresponding to the blood flow sequence in each transmission sequence group. In addition, a spectrum image of a blood flow in the tissue area of interest corresponding to each location of target sampling point groups is determined based on the target sampling point group corresponding to each first predetermined number of received second multi-beams. In this way, one frame spectrum image can be obtained while multiple frames of blood flow image are generated. Further, an ultrasonic system according to the embodiments of the present disclosure can simultaneously obtain a blood-flow-mode image and a spectrum image of blood flow velocity at a time.

In addition, in the present embodiment, the B-mode sequence in each of orderly transmitted transmission sequence groups corresponds to one subarea in the tissue area. One frame of blood-flow-mode image is obtained based on each transmission sequence group, while in order to obtain a frame of B-mode image corresponding to the tissue area, multiple transmission sequence groups are required, where the number of the required multiple transmission sequence groups is equal to the number of subareas forming the tissue area. Therefore, when one frame of B-mode image corresponding to the tissue area is obtained, multiple frames of blood-flow-mode image corresponding to the tissue area of interest can be obtained. Thereby, the present embodiment can solve the problem of non-fluency of blood-flow-mode images due to low frame rate in blood-flow-mode imaging in conventional technologies. Moreover, in the present embodiment, spectrum images at multiple positions in the tissue area of interest are determined. Thus, a blood flow image composited by a B-mode image and a blood-flow-mode image, and spectrum images of blood flows at multiple positions in the blood flow image can be simultaneously displayed at a time.

Figure 4:
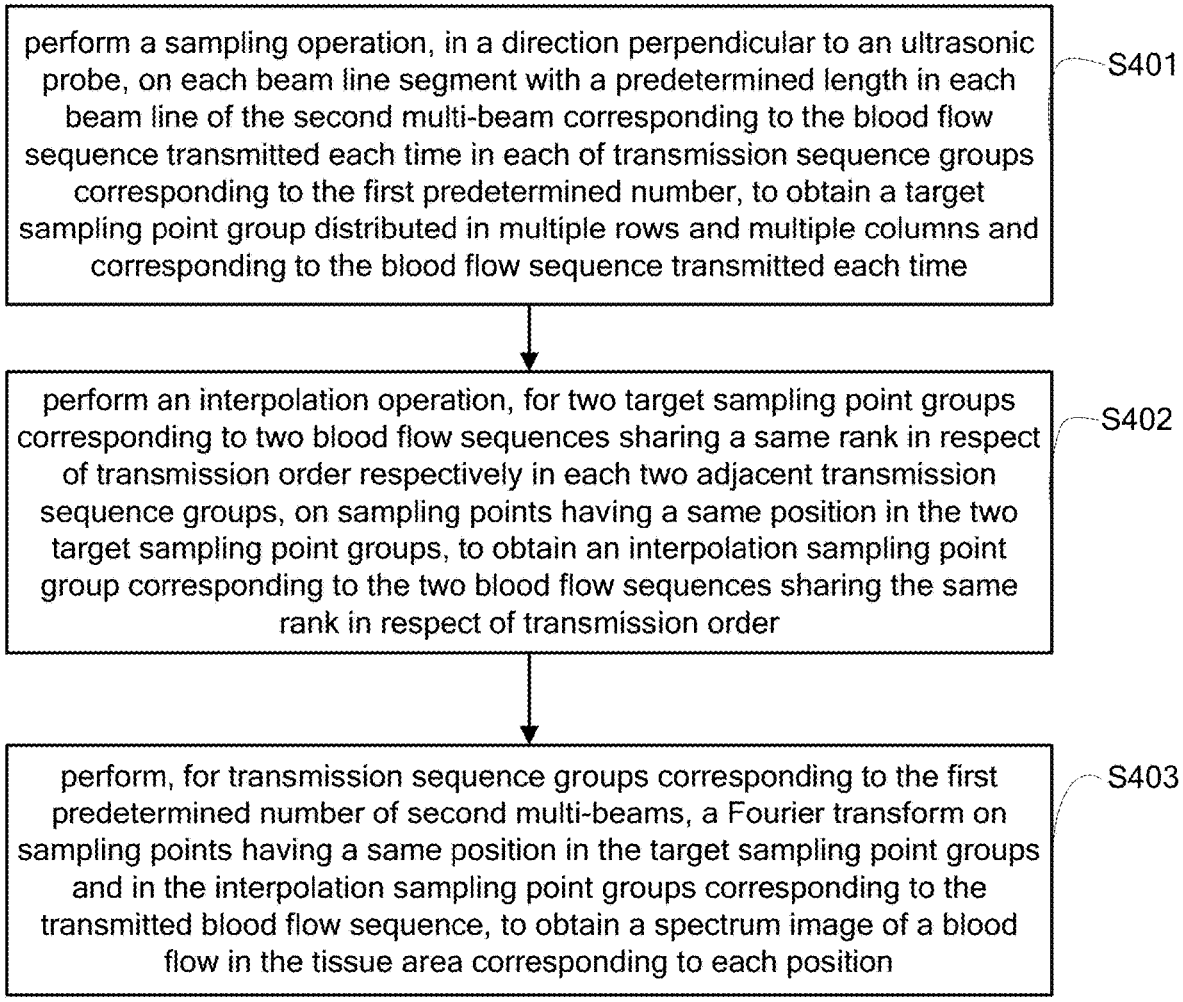
FIG. 4 is a flowchart of a method for determining a spectrum image of a blood flow in a tissue area of interest corresponding to each location of a target sampling point group according to an embodiment of the present disclosure.

Specifically, a flowchart of determining, based on target sampling point groups corresponding to each first predetermined number of received second multi-beams from the sequentially obtained second multi-beams, a spectrum image of a blood flow in the tissue area of interest corresponding to each position of the target sampling point groups according to a method embodiment is shown FIG. 4. The process of the method embodiment shown in FIG. 4 may include steps 401 to 403.

In step 401, a sampling operation is performed, in a direction perpendicular to an ultrasonic probe, on each beam line segment with a predetermined length in each beam line of the second multi-beam corresponding to the blood flow sequence transmitted each time in each of transmission sequence groups corresponding to the first predetermined number, to obtain a target sampling point group distributed in multiple rows and multiple columns and corresponding to the blood flow sequence transmitted each time.

In the present embodiment, during the process of sequentially receiving second multi-beams, whenever the number of received second multi-beams reaches the first predetermined number, a sampling operation is performed on each of the first predetermined number of second multi-beams in a predetermined manner to obtain a target sampling point group corresponding to each second multi-beam. Reference can be made to the specific process in step A1 shown in FIG. 1 for the specific implementation of performing the sampling operation on each second multi-beam to obtain the target sampling point group corresponding to the second multi-beam, which is not repeated herein.

In step 402, for two target sampling point groups corresponding to two blood flow sequences sharing a same rank in respect of transmission order respectively in each two adjacent transmission sequence groups, an interpolation operation is performed on sampling points having a same position in the two target sampling point groups, to obtain an interpolation sampling point group corresponding to the two blood flow sequences sharing the same rank in respect of transmission order.

It is assumed that the transmission sequence groups are sequentially A1, A2, A3, A4, A5 and A6, a current transmission sequence group is A3 and the first predetermined number is 3. Accordingly, in the present embodiment, a spectrum image of a blood flow at each position in the tissue area of interest is determined based on A1, A2 and A3, and a spectrum image of a blood flow at each position in the tissue area of interest is determined based on A4, A5 and A6. For example, in a case that multiple second multi-beams respectively corresponding to the sequence transmitted for multiple times in each of A1, A2 and A3 are obtained currently, spectrum images of blood flows at multiple positions in the tissue area of interest are determined based on the multiple second multi-beams corresponding to each of A1, A2 and A3.

Specifically, in the present step, interpolation sampling point groups corresponding to A1 and A2 and interpolation sampling point groups corresponding to A2 and A3 are sequentially determined. The specific process of determining the interpolation sampling point groups corresponding to A1 and A2 is the same as the specific process of determining the interpolation sampling point groups corresponding to A2 and A3, and in the present step, determination of the interpolation sampling point groups corresponding to the target sampling point groups included in transmission sequence groups A1 and A2 is described by taking A1 and A2 as an example. Each of A1 and A2 corresponds to multiple target sampling point groups corresponding to the blood flow sequence transmitted for multiple times. It is assumed that target sampling point groups corresponding to orderly transmitted blood flow sequences in A1 are sequentially M1, M2, M3, M4 and M5, and target sampling point groups corresponding to orderly transmitted blood flow sequences in A2 are sequentially N1, N2, N3, N4 and N5.

Specifically, the process of determining the interpolation sampling point groups corresponding to target sampling groups included in the transmission sequence group A1 and the transmission sequence group A2 is described as follows. An interpolation operation is performed on sampling points having a same position in M1 and N1, an interpolation operation is performed on sampling points having a same position in M2 and N2 . . . and an interpolation operation is performed on sampling points having a same position in M5 and N5. An interpolation sampling point group H1 corresponding to M1 and N1, an interpolation sampling point group H2 corresponding to M2 and N2 . . . and an interpolation sampling point group H5 corresponding to M5 and N1 are sequentially obtained. Specifically, the interpolation operation performed on two sampling points having a same position may be linear interpolation, cubic interpolation or other interpolations, which is not limited in the present embodiment.

In step 403, for transmission sequence groups corresponding to the first predetermined number of second multi-beams, a Fourier transform is performed on sampling points having a same position in the target sampling point groups and in the interpolation sampling point groups corresponding to the transmitted blood flow sequence, to obtain the spectrum image of the blood flow in the tissue area corresponding to each position.

After interpolation sampling point groups corresponding to the blood sequences sequentially transmitted in each two adjacent transmission sequence groups are obtained in step 301, where the target sampling point groups corresponding to A1 are M1, M2, M3, M4 and M5, the target sampling point groups corresponding to A2 are N1, N2, N3, N4 and N5 and the interpolation sampling point groups corresponding to A1 and A2 are H1, H2, H3, H4 and H5, in the present step, Fourier transforms are performed on multiple sampling points having a same position in the target sampling point groups and the interpolation sampling point groups corresponding to A1 and A2 and the target sampling point groups and the interpolation sampling point groups corresponding to A2 and A3 to obtain a spectrum of a blood flow at each position in the tissue area of interest, the multiple sampling points corresponding to the blood flow sequence transmitted at different time instants.

In the present embodiment, in order to ensure that the spectrum of blood flow velocity has a high temporal resolution, the number of sampling points is generally from 50 to 300. Therefore, in the present embodiment, one transmission sequence group corresponds to one frame of blood-flow-mode image and multiple transmission sequence groups correspond to one blood flow spectrum image. For example, in a case that five frames of blood-flow-mode image are determined, one blood flow spectrum image is determined. In addition, it is required to add a window to a signal before the Fourier transform is performed, to resolve a side lobe artifact produced, due to the fact that a length of the signal is small, in the spectrum of blood flow velocity during signal truncation. In the present embodiment, the window may be a Hamming window, or a Blackman window.

In the present embodiment, during determining spectrums of blood flows at multiple positions in the tissue area of interest based on the first predetermined number of transmission sequence groups, an interpolation operation is performed on sampling point groups corresponding to the blood flow sequence transmitted each time in each of each two adjacent transmission sequence group, to obtain an interpolation sequence group corresponding to the sequentially transmitted blood flow sequences in the two adjacent transmission sequence groups; and a Fourier transform is performed on sampling points at each position respectively in sampling point groups including the target sampling point groups and the interpolation sampling point groups corresponding to all of the first predetermined number of transmission sequence groups, to obtain the spectrum image of the blood flow at the position in the tissue area of interest. In the present embodiment, interpolation is first performed on the target sampling point groups corresponding to the transmission sequence groups, and a Fourier transform is performed on sampling points at a same position respectively in the target sampling point groups and the interpolation sampling point groups corresponding to each transmission sequence group to determine the spectrum of the blood flow at each position in the tissue area of interest. In this way, the accuracy of the spectrum of the blood flow at each position in the tissue area of interest as determined is improved in the present embodiment.

Figure 5:
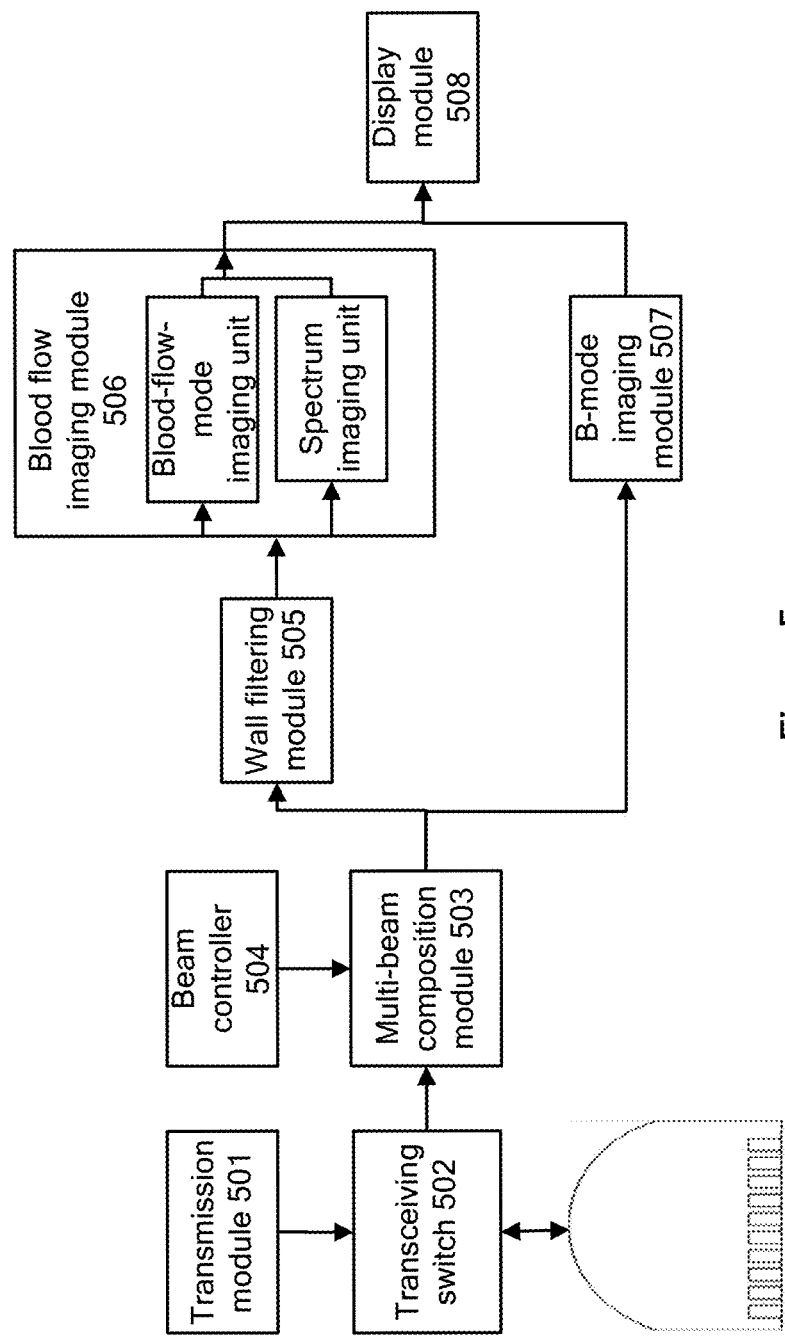
FIG. 5 is a schematic structural diagram of a device for simultaneously performing blood flow Doppler imaging and pulse Doppler imaging according to the present disclosure.

Reference is made to FIG. 5, which shows a schematic structural diagram of a device for simultaneously performing blood flow Doppler imaging and pulse Doppler imaging according to an embodiment of the present disclosure. The device includes a transmission module 501, a multi-beam composition module 503, a wall filtering module 505 and a blood flow imaging module 506.

The transmission module 501 is configured to, when a transceiving switch 502 is in a transmitting state, sequentially transmit each transmission sequence group, where in each transmission sequence group, a B-mode sequence is transmitted for once and a blood flow sequence is transmitted for multiple times after the B-mode sequence is transmitted.

The multi-beam composition module 503 is configured to, when the transceiving switch 502 is in a receiving state, sequentially receive a first echo signal group reflected by a tissue area of interest in response to the blood flow sequence transmitted each time in each transmission sequence group.

The multi-beam composition module 503 is further configured to, under the control of a beam controller 504, sequentially perform beam composition on the first echo signal group corresponding to the blood flow sequence transmitted each time, to obtain a first multi-beam corresponding to the blood flow sequence transmitted each time.

The wall filtering module 505 is configured to sequentially perform wall filtering on the first multi-beam corresponding to the blood flow sequence transmitted each time, to obtain a second multi-beam corresponding to the blood flow sequence transmitted each time, where the second multi-beam is a multi-beam representing a blood flow signal in the first multi-beam.

The blood flow imaging module 506 is configured to perform a blood-flow-mode imaging process and a blood flow spectrum imaging process based on sequentially obtained second multi-beams.

The blood flow imaging module 506 includes a blood-flow-mode imaging unit and a blood flow spectrum imaging unit. The blood-flow-mode imaging unit is configured to determine a frame of blood-flow-mode image based on the second multi-beam corresponding to the blood flow sequence in each transmission sequence group.

The blood flow spectrum imaging unit is configured to determine, based on target sampling point groups corresponding to each first predetermined number of received second multi-beams, a spectrum image of a blood flow in the tissue area of interest corresponding to each position of the target sampling point groups, where a target sampling point group corresponding to each second multi-beam is a sampling point group distributed in multiple rows and multiple columns and obtained by performing a sampling operation on each beam line of the second multi-beam in a predetermined manner.

The B-mode sequence transmitted by the transmission module 501 each time sequentially corresponds to one of a second predetermined number of subareas forming a tissue area. The transceiving switch 502 is further configured to sequentially receive a second echo signal group reflected by a corresponding subarea in response to the B-mode sequence transmitted each time. The multi-beam composition module 503 is further configured to sequentially perform multi-beam composition on the second echo signal group corresponding to the B-mode sequence transmitted each time, to obtain a third multi-beam corresponding to the B-mode sequence transmitted each time.

The B-mode sequence and the blood flow sequence are transmitted by the transmission module 501 in a non-focusing manner.

The device further includes a B-mode imaging module 507 and a display module 508.

The B-mode imaging module 507 is configured to determine, based on the third multi-beam corresponding to the B-mode sequence transmitted each time, a frame of B-mode image of the subarea in the tissue area corresponding to the B-mode sequence transmitted each time, and sequentially update, in a B-mode image corresponding to the tissue area, a B-mode image of the subarea corresponding to the B-mode sequence transmitted each time.

The display module 508 is configured to composite the blood-flow-mode image and the B-mode image to obtain a blood flow image; and display the blood flow image and a spectrum image of a blood flow at a user-specified position in the blood flow image. It should be noted that some or all the modules of the device for simultaneously performing blood flow Doppler imaging and pulse Doppler imaging can be implemented by using a processor 601 and a memory 602 as shown in FIG. 6, where instructions are stored on the memory 602, and the instructions, when executed by the processor, cause the processor 601 to perform the method for simultaneously performing blood flow Doppler imaging and pulse Doppler imaging.

The embodiments in this specification are described in a progressive way, each of which emphasizes the differences from others, and the same or similar parts among the embodiments can be referred to each other. In the present disclosure, relational terms such as "first" and "second" are merely used to distinguish one entity or operation from another entity or operation, but do not indicate or imply an actual relationship or order of these entities or operations. In the present disclosure, words such as "include", "comprise", and the like are inclusive rather than exclusive or exhaustive, which indicate "including but not limited to". Modifications, equivalents and improvements may further be made without departing from the spirit of the present disclosure, which shall all fall within the protection scope of the present disclosure.

With the description of the embodiments disclosed above, those skilled in the art can implement or use the technical solutions of the present disclosure. Numerous modifications to the embodiments are apparent to those skilled in the art, and the general principles defined herein may be implemented in other embodiments without departing from the spirit or scope of the present disclosure. Therefore, the present disclosure is not limited to the embodiments described herein, but should comply with the widest scope consistent with the principles and novel features disclosed herein.

The invention claimed is:

1. A method for simultaneously performing blood flow Doppler imaging and pulse Doppler imaging, comprising:
   sequentially transmitting each transmission sequence group, wherein in each transmission sequence group, a B-mode sequence is transmitted for once and a blood flow sequence is transmitted for a plurality of times after the B-mode sequence is transmitted;
   sequentially receiving a first echo signal group reflected by a tissue area of interest in response to the blood flow sequence transmitted each time in each transmission sequence group;

sequentially performing beam composition on the first echo signal group corresponding to the blood flow sequence transmitted each time, to obtain a first multi-beam corresponding to the blood flow sequence transmitted each time;

sequentially performing wall filtering on the first multi-beam corresponding to the blood flow sequence transmitted each time, to obtain a second multi-beam corresponding to the blood flow sequence transmitted each time, wherein the second multi-beam is a multi-beam representing a blood flow signal in the first multi-beam; and performing a blood-flow-mode imaging process and a blood flow spectrum imaging process based on sequentially obtained second multi-beams, wherein performing the blood-flow-mode imaging process comprises: determining a frame of blood-flow-mode image based on the second multi-beam corresponding to the blood flow sequence in each transmission sequence group, and performing the blood flow spectrum imaging process comprises: determining, based on target sampling point groups corresponding to each first predetermined number of received second multi-beams, a spectrum image of a blood flow in the tissue area of interest corresponding to each position of the target sampling point groups, wherein a target sampling point group corresponding to each second multi-beam is a sampling point group distributed in a plurality of rows and a plurality of columns and obtained by performing a sampling operation on each beam line of the second multi-beam in a predetermined manner, wherein determining, based on the target sampling point groups corresponding to each first predetermined number of received second multi-beams, the spectrum image of the blood flow in the tissue area of interest corresponding to each position of the target sampling point groups comprises:

performing a sampling operation, in a direction perpendicular to an ultrasonic probe, on each beam line segment with a predetermined length in each beam line of the second multi-beam corresponding to the blood flow sequence transmitted each time in each of transmission sequence groups corresponding to the first predetermined number, to obtain a target sampling point group distributed in a plurality of rows and a plurality of columns and corresponding to the blood flow sequence transmitted each time;

performing an interpolation operation, for two target sampling point groups corresponding to two blood flow sequences sharing a same rank in respect of transmission order respectively in each two adjacent transmission sequence groups, on sampling points having a same position in the two target sampling point groups, to obtain an interpolation sampling point group corresponding to the two blood flow sequences sharing the same rank in respect of transmission order; and performing, for transmission sequence groups corresponding to the first predetermined number of second multi-beams, a Fourier transform on sampling points having a same position in the target sampling point groups and in the interpolation sampling point groups corresponding to the transmitted blood flow sequence, to obtain the spectrum image of the blood flow in the tissue area corresponding to each position.

2. The method according to claim 1, wherein the B-mode sequence transmitted each time sequentially corresponds to one of a second predetermined number of subareas forming the tissue area, and the method further comprises:

sequentially receiving a second echo signal group reflected by a corresponding subarea in response to the B-mode sequence transmitted each time;

sequentially performing multi-beam composition on the second echo signal group corresponding to the B-mode sequence transmitted each time, to obtain a third multi-beam corresponding to the B-mode sequence transmitted each time;

determining, based on the third multi-beam corresponding to the B-mode sequence transmitted each time, a frame of B-mode image of the subarea in the tissue area corresponding to the B-mode sequence transmitted each time; and sequentially updating, in a B-mode image corresponding to the tissue area, a B-mode image of the subarea corresponding to the B-mode sequence transmitted each time.

3. The method according to claim 2, further comprising:

compositing the blood-flow-mode image and the B-mode image to obtain a blood flow image; and displaying the blood flow image and a spectrum image of a blood flow at a user-specified position in the blood flow image.

4. The method according to claim 1, wherein the transmitted B-mode sequence and the blood flow sequence are transmitted in a non-focusing manner.

5. A device, comprising:

a transmission module, configured to, when a transceiving switch is in a transmitting state, sequentially transmit each transmission sequence group, wherein in each transmission sequence group, a B-mode sequence is transmitted for once and a blood flow sequence is transmitted for a plurality of times after the B-mode sequence is transmitted;

a multi-beam composition module, configured to, when the transceiving switch is in a receiving state, sequentially receive a first echo signal group reflected by a tissue area of interest in response to the blood flow sequence transmitted each time in each transmission sequence group, wherein the multi-beam composition module is further configured to sequentially perform beam composition on the first echo signal group corresponding to the blood flow sequence transmitted each time, to obtain a first multi-beam corresponding to the blood flow sequence transmitted each time;

a wall filtering module, configured to sequentially perform wall filtering on the first multi-beam corresponding to the blood flow sequence transmitted each time, to obtain a second multi-beam corresponding to the blood flow sequence transmitted each time, wherein the second multi-beam is a multi-beam representing a blood flow signal in the first multi-beam; and a blood-flow-mode imaging module, configured to perform a blood-flow-mode imaging process and a blood flow spectrum imaging process based on sequentially obtained second multi-beams, wherein performing the blood-flow-mode imaging process comprises: determining a frame of blood-flow-mode image based on the second multi-beam corresponding to the blood flow sequence in each transmission sequence group, and performing the blood flow spectrum imaging process comprises: determining, based on target sampling point groups corresponding to each first predetermined number of received second multi-beams, a spectrum image of a blood flow in the tissue area of interest corresponding to each position of the target sampling point groups, wherein a target sampling point group corresponding to each second multi-beam is a sampling point group distributed in a plurality of rows and a plurality of columns and obtained by performing a sampling operation on each beam line of the second multi-beam in a predetermined manner, wherein determining, based on the target sampling point groups corresponding to each first predetermined number of received second multi-beams, the spectrum image of the blood flow in the tissue area of interest corresponding to each position of the target sampling point groups comprises:

performing a sampling operation, in a direction perpendicular to an ultrasonic probe, on each beam line segment with a predetermined length in each beam line of the second multi-beam corresponding to the blood flow sequence transmitted each time in each of transmission sequence groups corresponding to the first predetermined number, to obtain a target sampling point group distributed in a plurality of rows and a plurality of columns and corresponding to the blood flow sequence transmitted each time;

performing an interpolation operation, for two target sampling point groups corresponding to two blood flow sequences sharing a same rank in respect of transmission order respectively in each two adjacent transmission sequence groups, on sampling points having a same position in the two target sampling point groups, to obtain an interpolation sampling point group corresponding to the two blood flow sequences sharing the same rank in respect of transmission order; and performing, for transmission sequence groups corresponding to the first predetermined number of second multi-beams, a Fourier transform on sampling points having a same position in the target sampling point groups and in the interpolation sampling point groups corresponding to the transmitted blood flow sequence, to obtain the spectrum image of the blood flow in the tissue area corresponding to each position.

6. The device according to claim 5, wherein the B-mode sequence transmitted each time sequentially corresponds to one of a second predetermined number of subareas forming the tissue area, the transmission module is further configured to sequentially receive a second echo signal group reflected by a corresponding subarea in response to the B-mode sequence transmitted each time, the multi-beam composition module is further configured to sequentially perform multi-beam composition on the second echo signal group corresponding to the B-mode sequence transmitted each time, to obtain a third multi-beam corresponding to the B-mode sequence transmitted each time; and the device further comprises:

a B-mode imaging module, configured to determine, based on the third multi-beam corresponding to the B-mode sequence transmitted each time, a frame of B-mode image of the subarea in the tissue area corresponding to the B-mode sequence transmitted each time, and sequentially update, in a B-mode image corresponding to the tissue area, a B-mode image of the subarea corresponding to the B-mode sequence transmitted each time.

7. The device according to claim 6, wherein the device further comprises:

a display module, configured to: composite the blood-flow-mode image and the B-mode image to obtain a blood flow image; and display the blood flow image and a spectrum image of a blood flow at a user-specified position in the blood flow image.

8. The device according to claim 5, wherein the B-mode sequence and the blood flow sequence are transmitted by the transmission module in a non-focusing manner.

9. A method for simultaneously performing blood flow Doppler imaging and pulse Doppler imaging, comprising:

sequentially transmitting each transmission sequence group, wherein in each transmission sequence group, a B-mode sequence is transmitted for once and a blood flow sequence is transmitted for a plurality of times after the B-mode sequence is transmitted;

sequentially receiving a first echo signal group reflected by a tissue area of interest in response to the blood flow sequence transmitted each time in each transmission sequence group;

sequentially performing beam composition on the first echo signal group corresponding to the blood flow sequence transmitted each time, to obtain a first multi-beam corresponding to the blood flow sequence transmitted each time;

sequentially performing wall filtering on the first multi-beam corresponding to the blood flow sequence transmitted each time, to obtain a second multi-beam corresponding to the blood flow sequence transmitted each time, wherein the second multi-beam is a multi-beam representing a blood flow signal in the first multi-beam; and performing a blood-flow-mode imaging process and a blood flow spectrum imaging process based on sequentially obtained second multi-beams, wherein performing the blood-flow-mode imaging process comprises: determining a frame of blood-flow-mode image based on the second multi-beam corresponding to the blood flow sequence in each transmission sequence group, and performing the blood flow spectrum imaging process comprises: determining, based on target sampling point groups corresponding to each first predetermined number of received second multi-beams, a spectrum image of a blood flow in the tissue area of interest corresponding to each position of the target sampling point groups, wherein a target sampling point group corresponding to each second multi-beam is a sampling point group distributed in a plurality of rows and a plurality of columns and obtained by performing a sampling operation on each beam line of the second multi-beam in a predetermined manner, wherein determining the frame of blood-flow-mode image based on the second multi-beam corresponding to the blood flow sequence in each transmission sequence group comprises:

sequentially performing a sampling operation, in a direction perpendicular to an ultrasonic probe, on each beam line segment with a predetermined length in each beam line of each second multi-beam, to obtain a target sampling point group distributed in a plurality of rows and a plurality of columns and corresponding to the blood flow sequence transmitted each time in each transmission sequence group;

determining, for two target sampling point groups corresponding to the blood flow sequence transmitted at each two adjacent times and based on beam line segments to which two sampling points having a same position respectively in the two target sampling point groups belongs, a velocity of a blood flow at each same position, to obtain a velocity of a blood flow corresponding to the blood flow sequence transmitted at each two adjacent times at each same position;

determining, based on the velocity of the blood flow corresponding to the blood flow sequence transmitted at each two adjacent times at each same position, a movement velocity of a blood flow in the tissue area of interest corresponding to each same position; and determining, based on a correspondence relationship between each same position in the tissue area of interest and the movement velocity of the blood flow, the frame of blood-flow-mode image.

10. The method according to claim 9, wherein the B-mode sequence transmitted each time sequentially corresponds to one of a second predetermined number of subareas forming the tissue area, and the method further comprises:

sequentially receiving a second echo signal group reflected by a corresponding subarea in response to the B-mode sequence transmitted each time;

sequentially performing multi-beam composition on the second echo signal group corresponding to the B-mode sequence transmitted each time, to obtain a third multi-beam corresponding to the B-mode sequence transmitted each time;

determining, based on the third multi-beam corresponding to the B-mode sequence transmitted each time, a frame of B-mode image of the subarea in the tissue area corresponding to the B-mode sequence transmitted each time; and sequentially updating, in a B-mode image corresponding to the tissue area, a B-mode image of the subarea corresponding to the B-mode sequence transmitted each time.

11. The method according to claim 10, further comprising:

compositing the blood-flow-mode image and the B-mode image to obtain a blood flow image; and displaying the blood flow image and a spectrum image of a blood flow at a user-specified position in the blood flow image.

12. The method according to claim 9, wherein the transmitted B-mode sequence and the blood flow sequence are transmitted in a non-focusing manner.

* * * * *